United States Patent [19]

Malter

[11] Patent Number: 5,587,300
[45] Date of Patent: Dec. 24, 1996

[54] METHOD TO INCREASE REGULATORY MOLECULE PRODUCTION

[75] Inventor: James S. Malter, Madison, Wis.

[73] Assignee: Wisconsin Ulumni Research Foundation, Madison, Wis.

[21] Appl. No.: 233,130

[22] Filed: Apr. 26, 1994

[51] Int. Cl.$^6$ .......................... C12P 21/00; C12P 21/02; C12N 15/00; C12N 15/06
[52] U.S. Cl. .................. 435/69.1; 435/69.5; 435/69.51; 435/69.52; 435/172.3; 435/240.2; 435/320.1
[58] Field of Search ................................. 435/69.1, 69.5, 435/69.51, 69.52, 172.3, 240.2, 320.1

[56] References Cited

PUBLICATIONS

T. Aharon et al., "Selective Destabilization of Short–Lived mRNAs with the Granulocyte–Macrophage Colony–Stimulating Factor AU–Rich 3' Noncoding Region Is Mediated by a Cotranslational Mechanism", *Molecular and Cellular Biology*, 13(3), 1971–1980 (1993).

J. K. Burkholder et al., "Rapid transgene expression in lymphocyte and macrophage primary cultures after particle bombardment–mediated gene transfer", *J. Immunol. Methods.*, 165, 149–156 (1993).

P. Gillis et al., "The Adenosine–Uridine Binding Factor Recognizes the AU–rich Elements of Cytokine, Lymphokine, and Oncogene mRNAs", *J. Biol. Chem.*, 266(5), 3172–3177 (1991).

R. Higuchi, "Using PCR to Engineer DNA in *PCR Technology*": H. Erlich, Ed.; Stockton Press, New York, NY; 61–70 (1989), Chapter 6.

C. O. Jacob et al., "Disruption in the AU motif of the mouse TNF–α 3'UTR correlates with reduced TNF production by macrophages in vitro", *Nucleic Acids Research*, 21(11), 2761–2766 (1993).

T. R. Jones, et al., "Rapid Cytoplasmic Turnover of c–myc mRNA: Requirement of the 3' Untranslated Sequences", *Molecular and Cellular Biology*, 7(12), 4513–4521 (1987).

J. S. Malter, "Identification of an AUUUA–Specific Messenger RNA Binding Protein", *Science*, 246, 664–666 (1989).

J. S. Malter, et al., "A Redox Switch and Phosphorylation Are Involved in the Post–translational Up–regulation of the Adenosine–Uridine Binding Factor by Phorbol Ester and Ionophore", *J. Biol. Chem.*, 266 (5), 3167–3171 (1991).

J. S. Malter et al., "Adenosine–Uridine Binding Factor Requires Metals for Binding to Granulocyte–Macrophage Colony–Stimulating Factor mRNA", *Enzyme*, 44, 203–213 (1990).

J. S. Malter, Abstract of National Institute of Health Grant No. 5R01DK45213. This Abstract was obtained from the online DIALOG file Federal Research in Progress.

F. Meijlink, "Removal of a 67–base–pair sequence in the Noncoding region of protooncogene fos converts it to a transforming gene", *Proc. Natl. Acad. Sci. USA*, 82, 4987–4991 (1985).

T. Otsuka et al., "Isolation and Characterization of an Expressible cDNA Encoding Human IL–3 ", *J. Immunol.*, 140, 2288–2295 (1988).

I. J. Rondon et al., "Hypoxia Up–regulates the Activity of a Novel Erythropoietin mRNA Binding Protein", *J. Biol. Chem.*, 266 (25), 16594–16598 (1991).

S. Savant–Bhonsale et al., "Evidence for instability of mRNAs containing AUUUA motifs mediated through translation–dependent assembly of a >20S degradation complex", *Genes & Development*, 6, 1927–1939 (1992).

G. D. Schuler et al., "GM–CSF and Oncogene mRNA Stabilities Are Independently Regulated in trans in a Mouse Monocytic Tumor", *Cell*, 55, 1115–1122 (1988).

G. Shaw et al., "A Conserved AU Sequence from the 3'Untranslated Region of GM–CSF mRNA Mediates Selective mRNA Degradation", *Cell*, 46, 659–667 (1986).

J. M. Stephens et al., "Tumor Necrosis Factor α–induced Glucose Transporter (GLUT–1) mRNA Stabilization in 3T3–L1 Preadipocytes", *J. Biol. Chem.*, 267(12), 8336–8341 (1992).

A. Wodnar–Filipowicz et al., "Regulation of interleukin 3mRNA expression in mast cells occurs at the posttranscriptional level and is mediated by calcium ions", *Proc. Natl. Acad. Sci. USA*, 87, 777–781 (1990).

M. Akashi et al., "Number and Location of AUUUA Motifs: Role in Regulating Transiently Expressed RNAs," *Blood*, 83, 3182–3187 (Jun. 1, 1994).

T. Wilson et al., "Removal of poly(A) and consequent degradation of c–fos mRNA facilitated by 3' AU–rich sequences," *Nature*, 336, 396–399 (Nov. 1988).

Primary Examiner—James Martinell
Attorney, Agent, or Firm—Mueting, Raasch, Gebhardt & Schwappach, P.A.

[57] ABSTRACT

The present invention provides a method to increase the production of a regulatory molecule, i.e., a molecule that regulates cell behavior, such as a cytokine or a protooncogene, in a population of transfected cells, whether normal (resting or activated) or tumor cells. The method involves mutating a native or "wild type" cDNA sequence that encodes an mRNA sequence for a regulatory molecule to form a mutant cDNA sequence capable of producing a more stable mRNA sequence. Specifically, the method involves mutating a wild type cDNA sequence that encodes an unstable mRNA sequence for the regulatory molecule, wherein the mRNA includes a 3' untranslated region having a destabilizing element comprising an AUUUA sequence, to form a mutant cDNA sequence capable of producing a more stable mRNA sequence, wherein the AUUUA sequence is replaced by AUGUA, AUAUA, GUGUG, AGGGA, GAGAG, or a combination thereof; and transfecting a cell population with the mutant cDNA sequence so that the production of the regulatory molecule is enhanced by the cells.

25 Claims, 2 Drawing Sheets

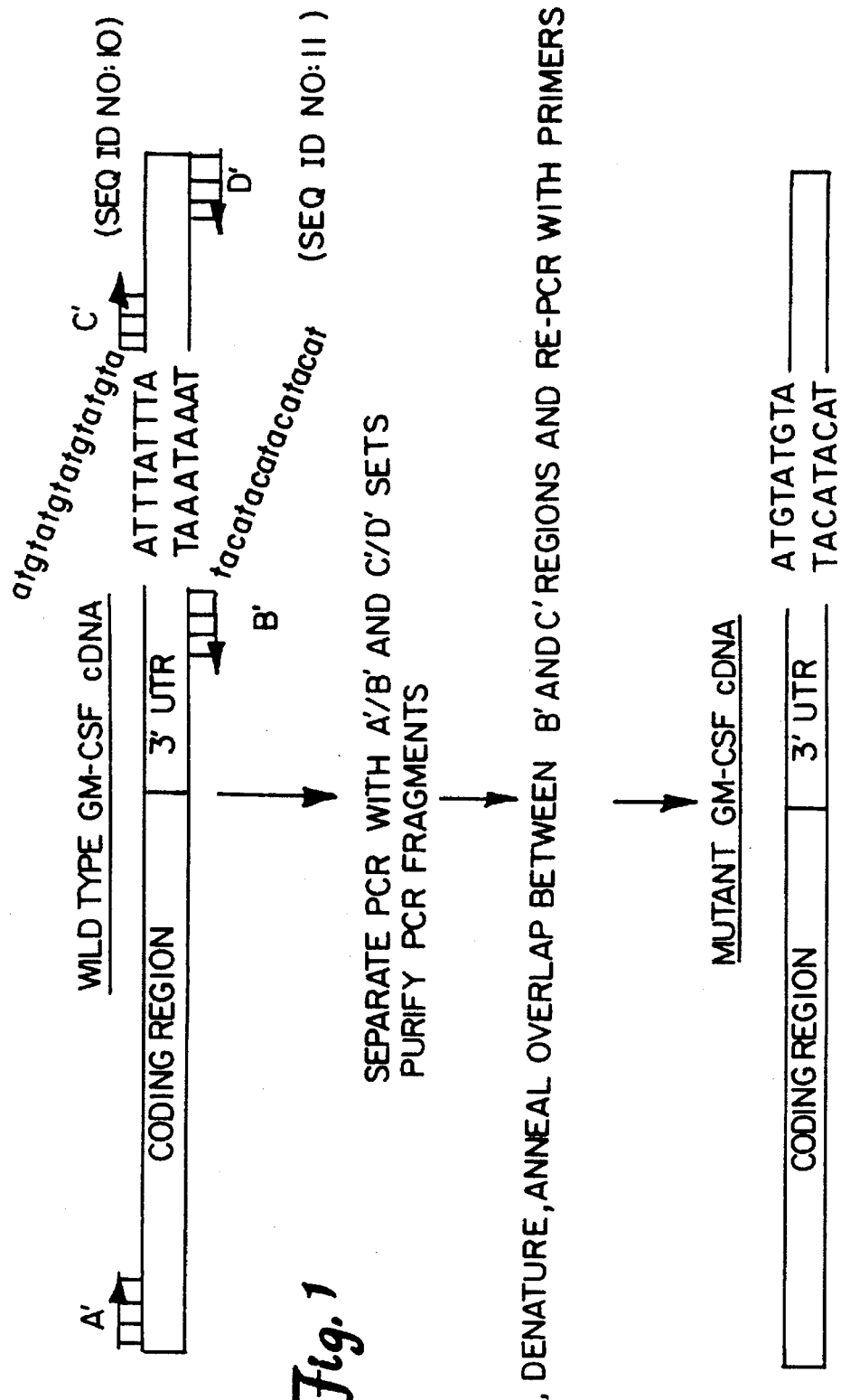

GM-CSF-1: 5' ATGTGGCTGCAGAGCCTGC 3' (SEQ ID NO: 2)
GM-CSF-2: 5' TACATACATACATACATATTACTGATTTCTGTCA 3' (SEQ ID NO: 3)
GM-CSF-3: 5' ATGTATGTATGTATTCAAGATGTTTTACC 3' (SEQ ID NO: 4)
GM-CSF-4: 5' AGAAGCATATTTTTAATAATA 3' (SEQ ID NO: 5)

Fig. 2A

IL-3-1: 5' CAGAGCCCCCACGAAGGA 3' (SEQ ID NO: 6)
IL-3-2: 5' TACATACATACATACATGAGAACACAACCGC 3' (SEQ ID NO: 7)
IL-3-3: 5' ATGTATGTATGTAGCAGAGAGGAGCCATGT 3' (SEQ ID NO: 8)
IL-3-4: 5 GTTCAGAGTCTAGTTTAT 3' (SEQ ID NO: 9)

Fig. 2B

METHOD TO INCREASE REGULATORY MOLECULE PRODUCTION

STATEMENT OF GOVERNMENT RIGHTS

This invention was made with the support of the U.S. Government under National Institutes of Health Grant No. R01-DK45213. The Government has certain rights in the invention.

BACKGROUND OF THE INVENTION

Cytokines are proteins released by lymphocytes, endothelial cells, neurons, glia, mononuclear cells and transformed or tumorigenic cells upon contact with specific antigens, proteins or other cells. Generally, they are important cell-cell communication and cellular regulation. More specifically, they affect the function of all cell types involved in the immune and hematopoietic systems. Furthermore, they have been implicated in the pathophysiology of a wide range of diseases. Examples of cytokines with therapeutic importance include interferons a and g, interleukins 1, 2, 3, 4, 6, 10 and 12, tumor necrosis factor a, colony stimulating factors (CSF) including granulocytemacrophage colony stimulating factor (GM-CSF), M-CSF and G-CSF, and erythropoietin.

Cytokines hold considerable promise for anti-cancer therapy. It is accepted that a local inflammatory response accompanied by anti-tumor activity can be induced by cytokines. GM-CSF, interleukins 2, 4, 6, and 12, as well as tumor necrosis factor a (TNF-a) have all shown considerable promise as anti-cancer therapeutics. Ideally, therapeutic cytokines would be induced at high levels only in the vicinity of the tumor. Unfortunately this goal has been impossible to achieve with systemic administration or even local infusion of proteinaceous cytokines. Difficulties with this approach included significant side effects, the great expense of the amounts required and imperfect delivery technology. In addition, cytokines expressed in vivo after gene transfer tend to be poorly expressed, despite their introduction in transcriptionally active expression constructs. The poor expression of cytokines after gene transfer has limited their widespread application in the treatment of cancer patients. The inability of cytokines to be expressed effectively in vivo likely reflects intrinsic cellular and molecular mechanisms which rigorously control cytokine production.

Protooncogenes are normal cellular genes which, upon loss of function, structure or regulation, can induce the conversion of normal cells into cancer cells. The loss of normal regulation typically involves genetic mutation such as chromosomal rearrangement. A variety of leukemias are well characterized for such rearrangements, with the most well known being the Philadelphia chromosome abnormality. In normal cells, protooncogenes regulate critical cell pathways which determine the growth rate, differentiation and cellular function. Classes of molecules known as tumor suppressing genes appear to act as anti-oncogenes by blocking the transforming effects of oncogene overexpression. At this time, the most obvious and best-supported use of protooncogene protein products would be as vaccines to elicit immune responses in patients who harbor tumors induced by oncogene overexpression. Thus, there may also be expanding uses for in vivo protooncogene expression after gene transfer.

A number of studies have demonstrated that post-transcriptional regulation is the dominant means that lymphoid and fibroblastic cells control cytokine expression. In resting cells, mRNAs for cytokines such as GM-CSF, interleukin 2, interleukin 3 or TNF-a are intrinsically unstable with decay rates ($T_{1/2}$) on the order of 20–40 minutes. This is primarily due to the presence of adenosine-uridine rich (AU-rich) sequence elements, or "ARE", located in the 3' untranslated region (UTR). For example, these AU-rich elements cause GM-CSF or interleukin 3 mRNAs to be rapidly degraded in the cytoplasm of resting cells. The rapid decay of mRNAs severely reduces mRNA accumulation and hence the amount of protein that can be produced.

The AU-rich elements are composed of multiple reiterations of the pentameric sequence adenosine-uridine-uridine-uridine-adenosine (AUUUA). In GM-CSF mRNA the AUUUA elements are present in tandem array (i.e., AUUUAUUUAUUUA (SEQ ID NO:1)) but this arrangement appears not to be obligatory. Other unstable cytokine mRNAs including interferon gamma, TNF-a and interleukin 6 contain AUUUA motifs which are dispersed throughout the 3' untranslated region. Removal of the AU-rich elements from GM-CSF mRNA led to increased stability of the mutant message while inclusion of the AU-rich element into the 3' untranslated region of the previously stable globin mRNA caused the latter to be rapidly decayed. These and other data have demonstrated that the AU-rich element causes cytokine mRNAs to be rapidly degraded in the cytoplasm of resting cells.

Protooncogene mRNAs often contain AU-rich elements which are identical to those in the cytokine mRNAs. Very little is known about the mechanisms which underlie the control of protooncogene mRNA stability. The inclusion of AU-rich elements in many of these molecules suggests that protooncogene mRNAs will be similarly if not identically regulated as cytokine mRNAs. In two systems, however (fos and myc) the AU-rich element functions in tandem with a poorly described second element located in the coding region. Either element appears sufficient to induce the rapid decay of fos or myc mRNA in resting cells.

Lymphocytes activated by phorbol esters, cytokines including interleukin 1 or TNF-a, or plant lectins (phytohemagglutinin-PHA) show dramatically increased levels of cytokine mRNA. This transcriptional upregulation, however, plays a minimal role in contributing to increased steady state levels of mRNA after cell activation. Instead, mRNA accumulation appears to be determined by a near complete inhibition of cytokine mRNA decay. Therefore, cells contain mechanisms which can attenuate or accelerate the decay of cytokine mRNAs to preserve appropriate cell function. This regulation appears to revolve around the AU-rich element and as discussed later, appears to be mediated by proteins which interact with it.

In an effort to understand how the degradation of mRNAs containing AU-rich elements are regulated, Malter et al. have assayed cytosolic lysates from activated cells for proteins which can bind to the AUUUA motif. They have described a protein factor which specifically interacts with this element and based upon its binding specificity for AUUUA motifs, denoted it the "AU-binding factor" or simply "AUBF." See J. S. Malter, *Science*, 246, 664–666 (1989); J. S. Malter et al., *J Biological Chemistry*, 226, 3167–3171 (1991); and P. Gillis et al., *J. Biological Chemistry*, 266, 3172–3177 (1991). AUBF specifically binds to multiple reiterations of the AUUUA sequence. This factor is not detectable in resting or quiescent cells (cells which have not entered the cell cycle) but it can be rapidly induced after cell activation with phorbol esters, lectins or cytokines. In addition, Malter et al. have detected constitutive AUBF activity in many tumor cell lines including those from lymphoid, fibroblastic or neural origin. Many of these same cell lines contain abnormally stable cytokine mRNAs.

The disruption of the AU-rich elements ("ARE") with a variety of nucleotide substitutions have been uniformly shown to stabilize the resultant cytokine mRNA. In all cases, the more stable mRNA accumulated to higher than wild type levels. However, the accumulated, mutant mRNA has not been shown to be efficiently translated. This has led a variety of investigators to propose that there is an inverse correlation between cytokine mRNA stability and translation. See, for example, Bhonsale et al., *Genes and Development*, 6, 1927 (1992). Thus, it is believed that the more stable the mRNA, the less it translates, which results in decreased production of the regulatory molecule, e.g., cytokines.

Additional work in which cytokine DNAs have been genetically engineered to be poorly translated by a mutation of the start codon or ribosome binding site, generally produced very stable cytokine mRNAs. This has furthered current thinking that the more stable cytokine mRNAs become, the more poorly translated they are.

Therefore, a need exists for a method to enhance the production of cytokines from stabilized mRNAs in a manner that can enhance the production of cytokines in cells or tissues.

SUMMARY OF THE INVENTION

The present invention provides a method to increase the production of a regulatory molecule, i.e., a molecule that regulates cell behavior, such as a cytokine or a protooncogene, in a population of transfected cells, whether normal (resting or activated) or tumor cells. The method involves mutating a native or "wild type" cDNA sequence that encodes an mRNA sequence for a regulatory molecule to form a mutant cDNA sequence capable of producing a more stable mRNA sequence. The "wild type" mRNA sequence, i.e., the mRNA sequence encoded by the native or "wild type" cDNA sequence, is generally unstable relative to the mutant mRNA sequence, e.g., having a decay rate ($T_{1/2}$) of less than about three hours, as a result of a destabilizing element or elements present in the 3'-untranslated region of the "wild type" mRNA. The method subsequently involves transforming, i.e., transfecting, a population of cells with the mutant cDNA sequence so that the production of the regulatory molecule by the cells is enhanced. The transfection can occur in vitro or in vivo with enhancement of regulatory molecule production. The target cell populations can be prokaryotic as well as eukaryotic, including mammalian cells, plant cells, yeast cells, etc. Preferably, the target cell populations are mammalian.

More specifically, the present invention involves identifying a wild type cDNA sequence encoding an unstable mRNA sequence wherein the instability is due to the instability determinant, i.e., destabilizing element, AUUUA, in the 3'-untranslated region of unstable "wild type" mRNA. Preferably, the instability is due to at least two, e.g., 2–8, AUUUA sequences in the 3'-untranslated region. The multiple AUUUA sequences can be in tandem array as in the sequence AUUUAUUUAUUUA (SEQ ID NO: 1). The cDNA is then mutated in vitro so that the resultant AUUUA sequences are replaced by sequences that permit the corresponding mRNA to resist binding by AU-binding factor, while still being efficiently translated into the desired regulatory molecule, e.g., cytokine. For example, at least one, and preferably all of the AUUUA sequences can be replaced by AUGUA, AUAUA, GUGUG, AGGGA, or GAGAG sequences or a combination thereof. Target cells, e.g., mammalian cells, are then transfected with the mutant cDNA, and the corresponding stabilized mRNA results in a substantially increased (e.g., at least about 5–10×) production of the target regulatory molecule. This enhanced production of the regulatory molecule was wholly unexpected in view of prior work suggesting that such stabilized mRNA molecules would be poorly translated in vivo.

In its broadest aspect, the present method can be applied to any cDNA coding for a protein whose mRNA contains destabilizing sequences. The examples hereinbelow employ cDNAs coding for cytokines which contain the AUUUA destabilizing determinant. Such cytokines include, but are not limited to, TNF alpha, interferons alpha, beta and gamma, interleukins 1 through 13, granulocyte macrophage colony stimulating factor (GM-CSF) and a variety of neuropeptides including nerve growth factor, and calcitonin. Protooncogenes including c-myc, c-fos, c-myb, c-sis, c-rel and others also fall into this class. There are approximately 50 to 100 mRNAs which might or do have medicinal applications which contain AUUUA repeats.

It is also believed that similar mutations in the 3' untranslated region of erythropoietin (Epo) messenger RNA increase the production of Epo in bioreactors or cells. Erythropoietin is a glycoprotein hormone of 34 kDa that stimulates the proliferation and differentiation of erythroid progenitor cells. The instability determinant for Epo is within the 3' untranslated region of Epo mRNA, specifically within the region from nucleotides 759 through 879. This destabilizing element is not based on AUUUA sequences. This region, however, can be substituted with an irrelevant sequence that stabilizes Epo mRNA, increases its steady state levels, and leads to enhanced Epo expression. Specifically, the method to increase the production of erythropoeitin in a population of transfected cells includes: mutating a wild type cDNA sequence that encodes an unstable mRNA sequence for erythropoietin, wherein the mRNA includes a 3' untranslated region having a destabilizing element within nucleotides 759–879, to form a mutant cDNA sequence capable of producing a more stable mRNA sequence, wherein the destabilizing element is replaced by neutral sequences of comparable length, for example, from actin or globin; and transfecting a cell population with the mutant cDNA sequence so that the production of erythropoietin is enhanced by the cells.

As used herein with respect to the mutant mRNA formed by the present method, the term "more stable" can be evaluated in terms of the increased levels of regulatory molecule, e.g., polypeptide (or "protein"), produced from the mutant mRNA as opposed to the "wild type" mRNA encoding the same polypeptide. Alternatively, or additionally, the stability of the mRNA can be evaluated in terms of the reduction in the ability of a specific mRNA binding protein, e.g., AUBF for mRNAs containing AU-rich elements, to bind to the wild type mRNA, as measured by assays described hereinbelow.

The present invention also includes within its scope expression vectors or casettes, e.g., phages, plasmids, viral vectors, and the like, containing the mutant cDNAs produced by the method of the present invention. Preferably, the expression vectors contain mutant GM-CSF or IL-3 cDNAs that encode for mutant mRNAs containing AUGUA for the AUUUA elements of the 3' untranslated region. The present invention also includes within its scope cell populations, e.g., stable cell lines, transfected with the mutant cDNA of the present invention. These cell populations produce the desired regulatory molecule at a higher level than do normal cells containing wild type cDNA.

BRIEF DESCRIPTION OF THE DRAWINGS

FIG. 1: Schematic of the procedure of the present invention for stabilizing mRNA and enhancing regulatory molecule production (SEQ ID NO:10, SEQ ID NO:11).

FIG. 2: Oligonucleotide sequences used in one embodiment of the method of the present invention. FIG. 2A shows the GM-CSF amplimer sets for PCR mutagenesis (SEQ ID NO:2, SEQ ID NO:3, SEQ ID NO:4, SEQ ID NO:5). The underlined sequences are complementary to GM-CSF. FIG. 2B shows the IL-3 amplimer sets for PCR mutagenesis (SEQ ID NO:6, SEQ ID NO:7, SEQ ID NO:8, SEQ ID NO:9). The underlined sequences are complementary to IL-3.

DETAILED DESCRIPTION OF THE INVENTION

The present invention provides a method to increase the production of a regulatory molecule, i.e., a molecule that regulates cell behavior, such as a cytokine or a protooncogene, in a population of transfected cells by stabilizing the unstable mRNA sequence for the regulatory molecule via targeted mutations of the 3' untranslated region ("UTR") of the mRNA. Specific application of this method involves stabilizing cytokine or protooncogene mRNA via targeted mutations within the AU-rich elements ("ARE") of the 3' untranslated region. The present method is exemplified by a demonstration that substitution of AUGUA for AUUUA sequences in the 3' UTR of GM-CSF or interleukin-3 has a positive effect on mRNA stability and gene expression. Therefore, it is expected that the effects of ARE mutation in cDNAs coding for protooncogenes also enhanced mRNA stability and translation. Mutant protooncogene cDNAs can be constructed in an analogous manner to cytokine cDNAs.

The preferred method for such mutagenesis is overlap-extension PCR. Other methods, including excision mutagenesis, linker-scanner methods, or restriction digestion/repair can also be used. The overall strategy with GM-CSF as an example is shown in FIG. 1. PCR primers are produced which are complementary to the 5' and 3' termini of the cDNA, which if used together would produce a full-length amplified fragment. Two internal primers are also produced (mutagenic PCR primers whose 3' 18 bases are complementary to the cDNA of interest immediately 5' or 3' of the AUUUA motifs). The 5' end of these mutagenic primers are complementary to one another and code for 4 consecutive AUGUA, AUAUA, GUGUG, AGGGA, or GAGAG repeats. These sequences can be inserted as pyrimidine to purine substitutions or adenosine to guanosine swaps in the AUUUA element to disrupt their interactions with AUBF.

PCR is performed on the cDNA in two successive steps. First, the 5' and 3' ends of the target cDNA are amplified with primers ½ and primers ¾ (see FIG. 1), effectively eliminating the AUUUA elements. After 30 cycles of PCR, amplified fragments are visualized and excised from ethidium bromide stained agarose gels. After purification on Qiagen beads, the amplified fragments are mixed together, denatured and allowed to anneal by their complementary ends. In order for this method to be successful, the calculated T⁰M of the overlap must be >35° C. Therefore, all of the overlaps contain ample sequence length or base composition to ensure this. After reannealing, Taq polymerase and the two terminal primers (primers ¼) are added to allow extension and amplification of full length mutant cytokine cDNA's. In addition, mutant cDNAs can be sequenced using PCR primers 1 and 4 to verify insertion of the appropriate sequences in place of the AUUUA motifs.

Mutagenized cDNA's are then inserted into expression or transcription vectors via the "T" tailing method. This permits rapid cloning of PCR fragments without the need for restriction enzyme digestion. The present expression vectors contain regulatory regions functional in mammalian cells, i.e., an upstream CMV promotor with downstream SV 40 splice and polyadenylation signals. These constructs are transcriptionally active in resting mammalian cells such as lymphocytes, fibroblasts, skin or tumor cell lines after their introduction into cells by transformation methods known to the art, such as microprojectible bombardment or viral transfection.

The mutations listed above display essentially no interaction, i.e., binding, with AUBF. The ability to interact with AUBF is a good indicator of protein overexpression. Mutant mRNAs can also be radiolabeled in vitro and used in RNA gel mobility shift assays, which involve transcribing radiolabeled cytokine RNAs in vitro by T7 RNA polymerase and incubating the products with cytosolic lysate derived from activated peripheral blood mononuclear cells or Jurkat cells under appropriate ionic conditions. After 10 minutes, RNAse T1 is added to cleave unprotected probe RNA followed by native or SDS-PAGE. AUBF-RNA complexes migrate with an aggregate molecular size of 42 Kd on SDS-PAGE. Binding to AUBF is very sensitive to modest changes within the AUUUA sequence. It is expected that all mutations produced in accord with this method will bind poorly or not at all to AUBF.

Preferably, the present method will be carried out so as to leave intact as much of the wild-type 3' UTR sequence as possible so as not to interfere with gene expression. A purely reductionist approach, for example deletion of the entire 3' UTR, often results in mRNAs which do not accumulate or are poorly translated. The unpredictability of gene expression is a major problem which the present method avoids.

The mutagenization of protooncogene cDNAs are technically more complex than GM-CSF since GM-CSF contains one concentrated block of AUUUA sequences which can be deleted and substituted with AUGUA or other mutations in one single PCR overlap step. Protooncogene cDNAs however, often contain well-spaced AUUUA containing regions which will be removed sequentially. This potentially permits a cassette mutagenization approach whereby the ARE(s) are changed, and inserted into a previously ARE deleted, cDNA backbone. This approach is simpler as many of these cDNAs are >4 Kb and difficult to prepare entirely by PCR. Therefore, either protocol described above will be applied to protooncogene cDNAs and mutagenized.

The mutant cDNAs of the present invention can be used to transform, i.e., transfect, tumor or normal cells, using any known method, e.g., electroporation, lipofectin, calcium phosphate, DEAE-Dextran, viral transfection and the like. Isolated total mRNA is used for northern blotting or cellular supernatant is used for ELISA of cytokine or protooncogene production. As protooncogene polypeptides are not usually extracellular, a 5' secretory signal will be inserted in frame, upstream of the normal coding sequence. This modification will direct the nascent protooncogene polypeptide into the Golgi for ultimate secretion. RNA isolation is via the acid-phenol method. A preselected amount, i.e., 10–20 mg of total RNA is electrophoresed on formaldehyde denaturing agarose gels prior to transfer nylon membranes. Blots are hybridized to radiolabeled cDNAs, washed and exposed to film to determine mRNA accumulation. Controls including stable, nonmutated mRNAs such as actin will be used to verify equal loading and transfer. Cells transfected with equal amounts of control, unmutated protooncogene cDNAs will also be evaluated to calculate the degree of enhancement the ARE mutations have produced. The control transfectants will also be analyzed by ELISA for the concentration of extracellular protein.

Cytokines that do not contain an AU-rich element in the 3' untranslated region of mRNA can also be produced in higher amounts using the general method of the present invention, i.e., by stabilizing the unstable mRNA sequence for the cytokine via targeted mutations of the 3' untranslated region of the mRNA. A specific example is that of erythropoietin.

The Hep 3B hepatoblastoma cell line, a human hepatoma line, constitutively produces small amounts of erythropoeitin (Epo) which can be significantly increased in response to hypoxia or cobaltous chloride. Enhanced Epo production was preceded by a lager increase in the steady state levels of Epo mRNA. Unexpectedly, the upregulation of Epo mRNA in response to hypoxia was only partially due to increased Epo transcription. Measurement of Epo mRNA turnover by actinomycin D treatment of Hep 3B cells demonstrated that the message was markedly stabilized with an increase in the half-time from 1.5 to approximately 7.5 hours. These data suggest that Epo expression is partially regulated at the post-transcriptional level. Furthermore, interaction between Epo mRNA at nucleotides 759–879 and the cytoplasmic Epo mRNA binding protein of 70 kDa described in I. J. Rondon and J. S. Malter et al., *J. Biol, Chem.*, 266, 16594–16598 (1991), which is incorporated herein by reference, indicates that this region of Epo mRNA defines important cis elements. Also, the activity of this protein ("ERBP" or erythropoeitin mRNA binding protein) can be increased by hypoxia, which demonstrates co-regulation by a stimulus known to stabilize Epo mRNA. In the absence of bound protein, the region from nucleotides 759 through 879 acts as a destabilizer of Epo mRNA and attenuates its accmnulation in cells. Therefore, removal of this element and substitution with an irrelevant sequence will stabilize Epo mRNA, increase its steady state levels, and lead to enhanced Epo secretion. Many neutral sequences can be inserted into this position including 3' UTR regions of comparable length from actin or globin.

The construction of Epo cDNA mutants is analogous to the construction of GM-CSF and IL-3 cDNA mutants described herein. Briefly, the 5' and 3' ends of the cDNA are amplified by PCR in separate tubes to eliminate the intervening instability element. Overlapping, complementary sequences introduced on the PCR amplimers are used to produce overlap extension in a subsequent reaction. The resulting mutant cDNA is then subcloned by standard means into an expression vector.

The invention will be further described by reference to the following detailed examples. These examples are offered to further illustrate the various specific and preferred embodiments and techniques. It should be understood, however, that many variations and modifications may be made while remaining with the scope of the present invention.

EXPERIMENTAL EXAMPLES

Example 1 cDNA Construction of Mutant GM-CSF and Interleukin 3 (IL-3)

cDNA coding for GM-CSF was obtained from the American Type Culture Collection, Rockville, Md. (ATCC No. 39754). Full length cDNA for IL-3 was obtained from Dr. Christoph Moroni, Department of Microbiology, University of Basel, Switzerland. The sequence is published by T. Osuka et al., *J. Immunol.*, 140, 2288 (1988) which is incorporated herein by reference. Mutagenesis of these constructs was performed by overlap extension polymerase chain reaction (PCR) (see FIG. 1 for schematic), as described by R. Higuchi in "Using PCR to Engineer DNA", *PCR Technology*; H. Erlich, ed.; Stockton Press; pp. 61–70 (1989), which is incorporated herein by reference. Briefly, oligonucleotides complimentary to opposite strands of the most 5' and 3' regions of GM-CSF and IL-3 cDNAs were, synthesized by standard phosphoramadite chemistry and designated herein as GM-CSF-1 and GM-CSF-4, IL-3-1 and IL-3-4 (see FIG. 2 for the sequences (SEQ ID NO:2, SEQ ID NO:5, SEQ ID NO:6, SEQ ID NO:9). These ranged from 17 to 24 bases in length and contained approximately 50% GC residues with calculated melting temperatures in the range of 45°–55° C. Mutagenic primers were constructed containing complimentary sequences to GM-CSF or IL-3 cDNAs immediately 5' or immediately 3' to the AUUUA repeats present in the 3' UTRs of these cDNAs. These oligonucleotides are designated herein as GM-CSF-2 and GM-CSF-3 or IL-3-2 and IL-3-3 (see FIG. 2 for these sequences (SEQ ID NO:3, SEQ ID NO:4, SEQ ID NO:7, SEQ ID NO:8). At the 5' end of the mutagenic oligomers were 17 bases consisting of 4 ATGTA or TACAT reiterations, respectively.

The goal of PCR with these primer sets was to introduce 4 tandem repeats of the sequence AUGUA and delete the original AUUUA repeats. PCR was performed on GM-CSF or IL-3 cDNA templates using primer sets GM-CSF-½; GM-CSF-¾; IL-3-½; and IL-3-¾, using a 92° C. denaturation for 1 minute, 44° C. annealing for 1 minute and extension at 72° C. for 30 cycles. PCR products were visualized by agarose gel electrophoresis with ethidium bromide staining as well as by absorbance at 260 nanometers. Twenty nanograms of the amplified fragments from the GM-CSF-½, and GM-CSF-¾ or IL-3-½ and IL-3-¾ PCR products were mixed together in the presence of primer set GM-CSF-1 and GM-CSF-4 for the amplification of GM-CSF or IL-3-1 and IL-3-4 for the production of mutant IL-3 cDNAs.

Prior to the addition of the primer sets mentioned above, the first 5 cycles were performed with the 5' and 3' amplified fragments as a 2-step PCR using an annealing temperature of 36° C. for 3 minutes prior to denaturation at 92° C. for 1 minute. Following these initial 5 cycles amplimers ¼ for GM or IL-3 were added and 35 subsequent cycles were performed, using a 3-step PCR with denaturation at 92° C. for 1 minute, annealing at 44° C. for 1 minute and extension at 72° C. for 1 minute. Products were visualized by agarose gel electrophoresis with ethidium bromide staining and the appropriate sized band of approximately 750 base pairs for GM-CSF and 950 base pair for IL-3 were visualized and excised from the gel.

These products were further purified by the Qiagen kit (obtained from Qiagen Corporation, Chatsworth, Calif.) and ligated into an EcoRV cut, T-tailed, CMV (cytomegalovirus)

driven expression vector with downstream SV40 polyA signals. Ligations were performed at 16° C. for 18 hours under standard conditions followed by electrotransformation of competent *E. coli* strain DH5a. Recombinants were identified by PCR screening using primers sets ¼. After the identification of recombinants, plasmids were produced at large scale by standard methods and purified by cesium chloride density centrifugation. See FIGS. 1 and 2 for description of the sequence of the construction of these recombinant GM-CSF and IL-3 expression factors.

Example 2

Preparation of Cell or Cell Cultures

Normal human peripheral blood mononuclear cells (PBMC) were obtained from healthy volunteer blood donors with appropriate consent. Approximately 200–500 ml of whole blood was removed to heparinized blood collection bags. Whole blood was diluted 1:1 with RPMI 1640 media without fetal calf serum and layered over ficoll-hypaque prior to centrifugation at 1200 rpm for 25 minutes. The white cells were carefully removed, transferred to 50 ml conical tubes and washed twice with phosphate buffered saline. The cells obtained were greater than 95% viable as assessed by trypan blue exclusion with yields of $6 \times 10^8$ cells per 500 ml whole blood starting material. The cells were then transferred into RPMI 1640 media containing 10% fetal calf serum and used immediately for transfection or stored overnight in a 5% $CO_2$ environment at 37° C. No differences were observed with cells used immediately or those cultured overnight.

Chinese hamster ovary cells (CHO cells) were maintained as a monolayer on plastic plates in DMEM media with 10% fetal calf serum, sodium pyruvate and glutamine at 37° C. in a 5% $CO_2$ humidified environment. Cultured cells were fed on each of the three prior days before transfection.

Example 3

Transfection of Cells or Animals with GM-CSF or IL-3 cDNA and RNA Analysis by Northern Blotting (A) Microprojectile Bombardment Particle bombardment mediated gene transfer was performed as described by J. Burkholder et al., *Journal of Immunological Methods*, 165, 149–156 (1993). Briefly, this method utilizes gold beads of approximately 1 micron in diameter which have been coated with cDNA. Coated gold beads (10 mg cDNA/$5 \times 10^6$ target cells) are layered on a mylar sheet and placed over the discharge orifice of the particle bombardment gun. Within the orifice is a 25000 volt capacitor which upon discharge creates a shock wave sufficient to accelerate the gold particles on the mylar sheet forward. The moving projectiles penetrate target cells or tissues and introduce the DNA into the cells. In order to transfect cell lines, they are typically coated or sown on a plastic dish, which is inverted and placed over the discharge orifice of the particle acceleration gun. Approximately 6–10% of the total target cell population is effectively transduced by this method.

For these studies, Chinese hamster ovary cells or quiescent normal PBMC were used without activation. After the transfection, $5 \times 10^6$ cells were resuspended or incubated in 1 ml of complete media (RPMI 1640 with 10% fetal calf serum) and returned to culture at 37° C. in a 5% $CO_2$ environment. At various times after transfection, cells were pelleted by centrifugation and lysed with 4M guanidinium isothiocyanate, then processed to isolate total RNA. The RNA was deproteinated and selectively isolated from DNA by the standard acid-phenol method and subsequently precipitated with ethanol. After resuspension in formamide, RNA was quantitated by absorbance at 260 nanometers and size separated on formaldehyde-agarose denaturing gels using standard techniques. RNAs were visualized after electrophoresis by ethidium bromide staining and typically present in near identical amounts from lane to lane.

(B) Northern Blotting

After washing the gel with DEP-treated water, the RNA was transferred to nylon support by vacuum transfer using a Pharmacia-LKB vacuum transfer system as described by the manufacturer. RNA was identified on the nylon filter by fluorescence visualization and noted to be completely transferred from the gel. Filters were baked at 65° C. for 30 minutes prior to prehybridization and hybridized using Amershams quik-hyb solution as described by the manufacturer.

Typically, prehybridizations were carried out for 30–60 minutes and hybridizations for 1.5–3 hours using GM-CSF or IL-3 specific cDNA radiolabeled probes at $10^6$ CPMs/ml hybridization buffer labeled by the random priming method to specific activities greater than $10^9$ CPMs/microgram DNA. Blots were washed twice in 2× SSC/0.1% SDS at room temperature for 15 minutes followed by high stringency washes at 60°–65° C. for 15 minutes in 0.1× SSC/ 0.1% SDS. Filters were exposed to film with two intensifying screens for 16–24 hours. To verify equal loading and transfer of the RNA, filters were also hybridized with GAPDH radiolabeled cDNA probes.

(C) Protein Assay

Supernatents from transfected cells were harvested at various times and growth factor production determined by GM-CSF or IL-3 specific ELISA kits as described by the manufacturer (R and D Systems). Briefly, the kits contain immobilized cytokine specific antibodies in 96 well microliter plate format. Supernatants are added neat or diluted to the 96 well plates, allowed to bind to the immobilized antibody, washed extensively, and a secondary anti-cytokine antibody which is coupled to a detectable label is added. After extensive washing, color development is visualized and with the use of a standard curve, the concentrations of cytokine in the unknown samples are determined. In all cases standard curves were simultaneously run to calculate cytokine concentrations in the transfected supernatant.

(D) AUBF Assay

AUBF (adenosine-uridine binding factor) assays are performed essentially as described by J. S. Malter, *Science*, 246, 664–666 (1989). Briefly, Jurkat cells (T cell leukemia line, human origin) are lysed with 0.5% NP-40, in 10 mM tris pH 7.5, 15 mM Kcl, 0.2 mM DTT, and 0.1 mM PMSF, at 4° C. for 5 minutes. Crude cytosol is prepared by centrifugation of lysed cells at 15000× g for 15 minutes at 4° C. The supernate is removed and snap frozen in a dry ice/ethanol bath, or used immediately for AUBF assay.

To determine AUBF activity, radiolabeled GM-CSF RNA is prepared by in vitro transcription using a GM-CSF cDNA template with an upstream T7 RNA polymerase promoter. Runoff transcripts of approximately 800 bases are prepared with specific activity of approximately $10^7$ CPMs/mg RNA. $5 \times 10^4$ CPMs of activity are incubated with 1 mg of cytosolic lysate in a buffer containing 10 mM Hepes pH 7.9, 15 mM KCl, 0.1 mM DTT, 2 mg E coli tRNA, and 10% glycerol in a total volume of 10 microliters. Assays are incubated at 30°

C. for 10 minutes prior to the addition 20 units RNAse T1 for 30 minutes at 37° C. Reactions are applied to 7% native acrylamide gels and electrophoresed at 200 volts for approximately 30 minutes. Afterward, the gels are dried and exposed to film. AUBF is detected by a gel mobility shift of the radiolabeled GM-CSF radiolabeled ligand.

(E) Results/Discussion

After swapping AUGUA for AUUUA elements, both wild type and mutant GM-CSF and IL-3 cDNAs were subcloned into expression vectors with a 5' CMV promoter-enhancer and a downstream SV40 polyadenylation signal. The mutant constructs (containing AUGUA motifs for the normally present AUUUA motifs) were initially transiently transfected by the standard DEAE-dextran-chloroquine method into proliferating but nonactivated Jurkat cells to verify subcloned cDNAs would be appropriately expressed. Jurkat is a human T cell leukemia line which produces IL-2 mRNA and IL-2 protein after activation with phorbol esters and a co-mitogen.

After the transfection of 10 micrograms of GM-CSF-AUGUA cDNA into Jurkat cells, their viability was >50%. Cells were maintained for an additional 30 hours prior to the addition of 5 micrograms/ml of actinomycin D to prevent further transcription. Total RNA was subsequently harvested at 0, 1.5 and 3 hours for northern blotting and determination of the rate of decay of GM-CSF-AUGUA mRNA. Based upon examination of the gel and filter, equal amounts of RNA were loaded in all lanes and transferred to the nylon filter.

Wild type GM-CSF mRNA displayed a half time of approximately 30 minutes after its introduction into T cell tumor lines. Mutant GM-CSF-AUGUA mRNA decayed with a half time of greater than 5 hours. Therefore, GM-CSF-AUGUA mRNA was at least 10 fold more stable than the wild type message.

The kinetics of mRNA accumulation from transfected GM-CSF-AUGUA constructs were investigated. For these studies, Chinese Hamster Ovary cells (CHO) cells were transiently transfected with GM-CSF-AUGUA or vector DNA alone by particle mediated gene transfer (see Example 3 above). After transfection >75% of the cells remained viable as assessed by trypan blue staining. At 8, 20, 26 and 32 hours after transfection, total CHO cell RNA was harvested and 10 micrograms analyzed for GM-CSF mRNA by northern blotting. Evaluation of the gel and filter revealed the RNA was intact and equally loaded and transferred to the nylon membrane. Autoradiography after hybridization with radiolabeled GM-CSF cDNA probes revealed specific signals only in cells transfected with GM-CSF-AUGUA but not with the vector control.

GM-CSF mRNA declined with first order kinetics which is consistent with expression patterns typically seen after transient transfection. Expression was maximal at 8 hours which showed gradual extinction to approximately 1/5–1/10 that level by 32 hours. The supernatant was pooled and assayed for GM-CSF protein. $10^6$ cells transfected with GM-CSF-AUGUA produced a 20 fold excess of protein. Because the cDNAs were transfected in identical vectors under comparable conditions, the increased accumulation of GM-CSF-AUGUA mRNA is believed to be the result of enhanced mRNA stability.

These studies were repeated in unstimulated normal peripheral blood mononuclear cells (PBMCs). Total RNA was isolated at 7 and 24 hours after transient transfection (by particle bombardment) with the wild type or mutant GM-CSF or IL-3 vectors and in the case of GM-CSF transfectants, supernatant were saved for assay of GM-CSF protein production. Autoradiography after northern blotting with GM-CSF or IL-3 radiolabeled probes of total RNA isolated from transfectants revealed approximately 25 fold excess GM-CSF mRNA or 50 fold excess IL-3 mRNA produced from the mutant compared to the wild type constructs.

In addition, the ELISA revealed that GM-CSF protein was secreted at 25 fold greater levels after the transfection of the mutant compared to the wild type construct. In this case, GM-CSF-AUGUA transfectants produced approximately 2.6 nanograms per ml GM-CSF protein compared to 96 pg/ml produced from cells transfected with the wild type construct. These data demonstrate that normal resting human PBMC, like tumor cell lines, CHO or Jurkat cells also selectively over-accumulate GM-CSF-AUGUA or IL-3-AUGUA mRNAs compared to wild type messages. Unexpectedly and importantly, PBMC, like transfected CHO cells also secrete markedly enhanced amounts of GM-CSF protein (and probably IL-3) in direct correlation to the amount of mRNA present. Therefore, the mutant GM-CSF mRNA appears to be translated at least as well as the wild type mRNA. This is a totally unexpected result based on prior observations concerning the regulation of wild type GM-CSF mRNA decay and translation.

While the in vitro studies are important, they do not demonstrate if such constructs will be effective when used in vivo. In order to answer this question, human, wild-type (AUUUA) or mutant (AUGUA)GM-CSF cDNAs were introduced into mouse skin by particle acceleration. Mouse (Balb C) abdominal skin was treated with a depilatory, washed, and bombarded at 20 kV with 0.95 micrometer gold beads coated with identical amounts of GM-AUUUA, GM-AUGUA or a vector containing luciferase reporter cDNA ("control"). Three mice were employed per experiment to evaluate reproducibility. No untoward effects were observed in treated animals other than a slight rash at the "blast" site. Serum samples were taken from animals at 7 and 24 hours, and at 24 hours the bombarded skin was harvested and homogenized to obtain a total volume of 1 ml tissue extract. Both serum and skin samples were assayed by human GM-CSF specific ELISA to determine expression levels of the various transgenes.

| Mouse | A(450) | Serum [GM-CSF] |
|---|---|---|
| w.t. GMCSF | | |
| 1 (neat serum) | 0.019 | |
| 2 (neat serum) | 0.038 | |
| 3 (neat serum) | 0.035 | |
| Mean | 0.031 | 8 pg/ml |
| GMCSF-AUGUA | | |
| 1 (diluted 1/100) | 0.378 | |
| 2 (diluted 1/100) | 0.402 | |
| 3 (diluted 1/100) | 0.359 | |
| Mean | 0.380 | 650 pg/ml |
| Control | | |
| 1 | 0.027 | |
| 2 | 0.069 | |
| Mean | 0.048 | <8 pg/ml |

The ELISA has a linear range of 20 to 320 picograms/ml, with a lower limit of sensitivity of approximately 8 pg/ml. The cumulative serum data are shown above. Skin extracts obtained at 24 hours after human GM-AUGUA introduction contained human GM-CSF immunoreactive material at >32 nanograms/ml or approximately 100 U/ml. Identically prepared samples of skin bombarded with the wild-type construct had an average concentration of 0.33 nanograms/ml or approximately 1 U/ml. Serum samples 24 hours after transfection with GM-AUGUA contained GM-CSF at 650 picograms or 2 U/ml while the wild-type construct failed to produce detectable GM-CSF in the serum (<8 picograms/ml). Animals bombarded with luciferase control constructs also failed to produce detectable GM-CSF. These data unequivocally demonstrate that the GM-CSF protein detected in these experiments originated from the transgene. Second, they show that mutant GM-CSF constructs are extremely active in vivo at levels (100 U/ml) at least 100 fold greater than wild-type GM-CSF cDNAs.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one of skill in the art will be included within the invention defined by the claims.

What is claimed is:

1. A method to increase the production of a regulatory molecule in a population of transfected cells comprising:
   (a) mutating a wild type cDNA sequence that encodes a first mRNA sequence for the regulatory molecule, wherein the mRNA includes a 3' untranslated region having a destabilizing element comprising an AUUUA sequence, to form a cDNA sequence that encodes a second mRNA sequence more stable than the first mRNA sequence, wherein the AUUUA sequence is replaced by AUGUA, AUAUA, GUGUG, AGGGA, GAGAG, or a combination thereof; and
   (b) transfecting a cell population with the mutant cDNA sequence so that the production of the regulatory molecule by the cells is greater than the production of the regulatory molecule by a cell population with the wild type cDNA sequence.

2. The method of claim 1 wherein the first mRNA sequence comprises at least two AUUUA sequences.

3. The method of claim 2 wherein the first mRNA sequence comprises 2–8 AUUUA sequences.

4. The method of claim 2 wherein the AUUUA sequences are joined in adjacent to one another.

5. The method of claim 1 wherein the cell population is a mammalian cell population.

6. The method of claim 1 wherein the regulatory molecule is a cytokine.

7. The method of claim 6 wherein the cytokine is TNF-alpha, interferon-alpha, interferon-beta, inteferon-gamma, interleukins 1 through 13, granulocyte macrophage colony stimulating factor (GM-CSF), nerve growth factor, calcitonin.

8. The method of claim 1 wherein the regulatory molecule is a protooncogene.

9. The method of claim 8 wherein the protooncogene is c-myc, c-fos, c-myb, c-sis, or c-rel.

10. The method of claim 1 wherein the cell is transfected by microprojectile bombardment.

11. The method of claim 1 wherein the cell is transfected by viral transfection.

12. The method of claim 1 wherein the second mRNA sequence binds to AU-binding factor to a lesser extent than does the first mRNA sequence.

13. The method of claim 1 wherein the cells are normal resting cells.

14. The method of claim 1 wherein the regulatory molecule is GM-CSF.

15. The method of claim 1 wherein the regulatory molecule is IL-3.

16. An expression vector produced by the method comprising: mutating a cDNA sequence that encodes an mRNA sequence for a cytokine, wherein the mRNA sequence includes a sequence selected from the group consisting of AUGUA, AUAUA, GUGUG, GAGAG, AGGGA, and combinations thereof, in the 3' untranslated region in place of at least one AUUUA sequence and expression vectors that are the progeny of said vector.

17. The expression vector of claim 16 wherein the cytokine is GM-CSF.

18. The expression vector of claim 16 wherein the mutant cDNA sequence encodes an mRNA sequence containing an AUGUA sequence.

19. The expression vector of claim 16 wherein the cytokine is IL-3.

20. The expression vector of claim 19 wherein the mutant cDNA sequence encodes an mRNA sequence containing an AUGUA sequence.

21. A transfected cell line produced by the method comprising:
   (a) mutating a cDNA sequence that encodes an mRNA sequence for a cytokine, wherein the mRNA sequence includes a sequence selected from the group consisting of AUGUA, AUAUA, GUGUG, GAGAG, AGGGA, and combinations thereof, in the 3' untranslated region in place of at least one AUUUA sequence; and
   (b) transfecting a cell population with the mutant cDNA sequence.

22. The transfected cell line of claim 21 wherein the cytokine is GM-CSF.

23. The transfected cell line of claim 22 wherein the mutant cDNA sequence encodes an mRNA sequence containing an AUGUA sequence.

24. The transfected cell line of claim 21 wherein the cytokine is IL-3.

25. The transfected cell line of claim 24 wherein the mutant cDNA sequence encodes an mRNA sequence containing an AUGUA sequence.

* * * * *

UNITED STATES PATENT AND TRADEMARK OFFICE
CERTIFICATE OF CORRECTION

PATENT NO.: 5,587,300
DATED: December 24, 1996
INVENTOR(S): James S. Malter

It is certified that error appears in the above-identified patent and that said Letters Patent is hereby corrected as shown below:

Column 2, line 62, delete "226" and insert --266-- therefor;
Column 5, line 61, delete "filagments" and insert --fragments-- therefor;
Column 7, line 45, delete "accmnulation" and insert --accumulation-- therefor;
Column 8, line 29, delete "complimentary" and insert --complementary-- therefor;
Column 11, line 55, delete "supematant" and insert --supernatant-- therefor;
Column 11, line 67, delete "supernatant" and insert --supernatants-- therefor; and
Column 17, line 54, delete "factor, calcitonin" and insert --factor, or calcitonin-- therefor.

Signed and Sealed this

Twenty-fourth Day of March, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:1:

AUUUAUUUAU UUA 13

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

ATGTGGCTGC AGAGCCTGC 19

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TACATACATA CATACATATT ACTGATTTCT GTCA 34

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

ATGTATGTAT GTATGTATTC AAGATGTTTT ACC 33

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AGAAGCATAT TTTAATAAT A    21

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CAGAGCCCCA CGAAGGA    17

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TACATACATA CATACATGAG AACACAACCG C    31

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ATGTATGTAT GTATGTAGCA GAGGAGCCAT GT    32

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GTTCAGAGTC TAGTTTAT    18

( 2 ) INFORMATION FOR SEQ ID NO:10:

( i ) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

ATGTATGTAT GTATGTA 17

(2) INFORMATION FOR SEQ ID NO:11:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

TACATACATA CATACAT 17